(12) United States Patent
Bartnicki et al.

(10) Patent No.: US 10,023,870 B2
(45) Date of Patent: Jul. 17, 2018

(54) DNA APTAMERS BINDING THE HISTIDINE TAG AND THEIR APPLICATION

(71) Applicant: UNIWERSYTET JAGIELLONSKI, Cracow (PL)

(72) Inventors: Filip Bartnicki, Cracow (PL); Ewa Kowalska, Cracow (PL); Katarzyna Pels, Luzna (PL); Wojciech Strzalka, Cracow (PL)

(73) Assignee: UNIWERSYTET JAGIELLONSKI, Cracow (PL)

( * ) Notice: Subject to any disclaimer, the term of this patent is extended or adjusted under 35 U.S.C. 154(b) by 179 days.

(21) Appl. No.: 14/780,635

(22) PCT Filed: May 17, 2014

(86) PCT No.: PCT/PL2014/050026
§ 371 (c)(1),
(2) Date: Sep. 28, 2015

(87) PCT Pub. No.: WO2014/185802
PCT Pub. Date: Nov. 20, 2014

(65) Prior Publication Data
US 2016/0060631 A1   Mar. 3, 2016

(30) Foreign Application Priority Data
May 17, 2013 (PL) ........................................ 403939

(51) Int. Cl.
| C12N 15/115 | (2010.01) |
| C07K 1/22 | (2006.01) |
| C07K 7/08 | (2006.01) |
| C07K 14/00 | (2006.01) |

(52) U.S. Cl.
CPC .............. *C12N 15/115* (2013.01); *C07K 1/22* (2013.01); *C07K 7/08* (2013.01); *C07K 14/001* (2013.01); *C12N 2310/16* (2013.01)

(58) Field of Classification Search
CPC .......... C07K 14/001; C07K 1/22; C07K 7/08; C12N 15/115; C12N 2310/16
See application file for complete search history.

(56) References Cited

U.S. PATENT DOCUMENTS 7,329,742 B2 * 2/2008 Doyle .................. C12N 15/115
435/283.1

FOREIGN PATENT DOCUMENTS

| CN | 102719430 A | 10/2012 | ............. C12N 15/11 |
| CN | 102229932 A | 11/2012 | ............. G01N 33/68 |
| WO | WO 2005/024042 A2 | 3/2005 | |

OTHER PUBLICATIONS

Bartnicki et al., "Imidazole-free purification of His3-tagged recombinant proteins using ssDNA aptamer-based affinity chromatography," J. Chromatography A, 2015, vol. 1418, pp. 130-139.*
Kokpinar et al.; *Aptamer-Based Downstream Processing Of His-Tagged Proteins Utilizing Magnetic Beads*; Biotechnology And Bioengineering, vol. 108, No. 10; Oct. 12, 2011; pp. 2371-2379.
Lee et al.; *Coomassie blue is sufficient for specific protein detection of aptamer-conjugated chips*; Bioorganic & Medicinal Chemistry Letters; Pergamon, Amsterdam, NL, vol. 22, No. 4; Jan. 6, 2012, pp. 1520-1522.
Tan et al.,; *Molecular Beacon Aptaniers for Direct and Universal Quantitation of Recombinant Proteins from Cell Lysates*; Analytical Chemistry, vol. 84, No. 19; Oct. 2, 2012, pp. 8272-8276.
Walter et al.; *Systematic Investigation of Optimal Aptamer Immobilization for Protein-Microarray Applications*; Analytical Chemistry, vol. 80, No. 19; Oct. 1, 2008, pp. 7372-7378.
Tsuji et al.; *RNA aptamer binding to polyhistidine-tag*; Biochemical and Biophysical Research Communications, Academic Press Inc.; Orlando, FL US, vol. 386, No. 1; Aug. 14, 2009, pp. 227-231.
Shin et al.; *An alternative to Western blot analysis using RNA aptamer-functionalized quantum dots*; Bioorganic & Medicinal Chemistry Letters, vol. 20, No. 11; Jun. 1, 2010, pp. 3322-3325.
Lubbecke et al.; *Aptamers as detection molecules on reverse phase protein microarrays for the analysis of cell lysates*; Engineering In Life Sciences, vol. 12, No. 2; Apr. 25, 2012, pp. 144-151.
Hyun Kyung Lim et al.; *Aptamer-Based Alternatives To The Conventional Immobilized Metal Affinity Chromatography For Purification Of His-Tagged Proteins*; Analytical Letters, vol. 46, No. 3; Jan. 22, 2013, pp. 407-415.
Murphy et al.,; *An improved method for the in vitro evolution of aptamers and applications in protein detection and purification*; Nucleic Acids Research 2003, vol. 31, No. 18, e110.
Song et al.; *Aptamers and Their Biological Applications*; Sensors 2012, vol. 12; Jan. 9, 2012, pp. 612-631.
Vasseur et al.; *Solid-Phase Chemical Synthesis of 5'-Triphosphate DNA RNA, and Chemically Modified Oligonucleotides*; Current Protocols in Nucleic Acid Chemistry; 2012; 50:1.28.1-1.28.16.
Pon; *A Long Chain Biotin Reagent For Phosphoramidite The Automated Synthesis of 5'-Biotinylated Oligonucleotides*; Tetrahedron Lett. 1991; 32: 1715-1718.
International Search Report dated Sep. 8, 2014 in corresponding application No. PCT/PL2014/050026.
Written Opinion dated Sep. 8, 2014 in corresponding application No. PCT/PL2014/050026.
Polish Search Report dated Aug. 8, 2013 in corresponding application P.403939.

* cited by examiner

*Primary Examiner* — Galina Yakovleva
(74) *Attorney, Agent, or Firm* — Renner Kenner Greive Bobak Taylor & Weber

(57) ABSTRACT

A DNA aptamer was obtained which has an affinity for His-tag, and contains a nucleotide sequence selected from SEQ ID No. 1 and SEQ ID No. 2, which has clear applications.

1 Claim, 1 Drawing Sheet

DNA APTAMERS BINDING THE HISTIDINE TAG AND THEIR APPLICATION

CROSS-REFERENCE TO RELATED APPLICATION

This is a § 371 application of International Patent Application No. PCT/PL2014/050026, filed May 17, 2014.which claims benefit of Polish Patent Application No. P.403939, filed on May 17, 2013,and which is incorporated herein by reference.

INCORPORATION OF THE SEQUENCE LISTING

The official copy of the Sequence Listing is submitted concurrently with the specification as an ASCII formatted text file via EFS-Web, with a file name of "SEQUENCE-LISTINGascii.txt," a creation date of Sep. 28, 2015 and a size of 607 bytes. The Sequence Listing has only minor formatting changes relative to the Sequence Listing with the file name "eolf-seql.app," which is believed to have a creation date of Feb. 6, 2014 and a size of 607 bytes, that was filed with International Application No. PCT/PL2014/050026 on May 17, 2014, which claims priority of Polish application P.403939 filed May 17, 2013 wherein the Sequence Listing was disclosed in the Priority Document. The Sequence Listing filed via EFS-Web is part of the specification and is hereby incorporated in its entirety by reference herein.

TECHNICAL FIELD

The invention described below involves unique nucleotide sequences of single-stranded DNA aptamers binding a histidine tag and their application.

BACKGROUND OF INVENTION

Prokaryotic and eukaryotic cells are often used as efficient expression systems for the production of recombinant proteins. To obtain proteins which are of satisfactory purity and quality affinity chromatography methods are very often employed. An example of such chromatography is immobilized metal affinity chromatography (IMAC). To use this technology a short histidine tag (His-tag), composed usually of six successive repetitions of histidine residue must, be fused with the target protein. The His-tag can reversibly bind to certain metal ions (e.g. cobalt, copper, nickel and zinc). Using an appropriate carrier containing one of these ions the purification or immobilisation of His-tag proteins is possible. A His-tag attached to recombinant proteins can be used to detect them by the western blotting technique, using mono- or polyclonal antibodies directed against the tag. This protein detection system can be used in other in vitro techniques which are used to study interactions between proteins, such as pull down, co-immunoprecipitation or Far Western blotting.

DNA aptamers are defined as single-stranded deoxyribonucleic acid molecules of about 40-100 nucleotides in length, which have the ability to bind a ligand with high specificity and affinity. The rich secondary and tertiary structures of the aptamer mean that the matching of a selected aptamer with a target molecule is optimal.

The objective of this invention is to provide a new method for the identification of molecules containing a histidine tag, in particular through the provision of new molecules with a strong affinity for a molecular target containing a histidine tag, or any molecule (e.g., peptide, protein, DNA derivative) containing a histidine hexamer.

The technical aim specified above may be implemented in accordance with the discussed invention.

SUMMARY OF INVENTION

The subject of the invention is DNA aptamer with an affinity for a

His-tag aptamers, with the following nucleotide sequence 5'-

```
                                    (SEQ ID NO: 1)
5'-GTTTGCCGGTGGGCAGGTCTAGGGTCTGCTCGGGATTGCGGAGGAA
CATGCGTCGCAAAC-3'
``` hence forth called "aptamer A1", or the nucleotide sequence 5'-

```
                                    (SEQ ID NO: 2)
5'-GTTTGCCGGTGGGCAGGTTTAGGGTCTGCTCGGGATTGCGGAGGAA
CATGCGTCGCAAAC-3'
``` hence forth called "aptamer B1".

The invention allows, some variation in DNA sequences, provided that their affinity for the peptide or protein containing the His-tag is retained, and permits the selective purification of His-tag proteins from a mixture of several proteins. In particular, the scope of the invention covers variants of the above sequences which differ in at least one purine or pyrimidine base.

Another subject of the invention is the use of oligonucleotides with one of the sequences defined above for the preparation of molecules with an affinity for molecular targets, which contain a His-tag.

The use may be as follows:

for use as an alternative to antibodies directed against the His tag, to detect molecular targets containing the His tag, to purify molecular targets containing the His tag, to bind molecular targets containing the His tag, or to analyze the concentration of molecular targets containing the His tag.

In particular, these oligonucleotides may be used in the form of molecules with attached tags, e.g., a fluorescent tag to label the molecular targets possessing the His-tag.

These types of molecules can be used for example, to monitor interactions between proteins using spectroscopic techniques known to specialists such as FRET (Forster resonance energy transfer) or BiFC (bi-molecular fluorescence complementation).

The following may further clarify features of the invention:

BEST MODE FOR CARRYING OUT THE INVENTION

This description is supplemented by the working examples quoted below. They do not represent the full scope of this invention.

EXAMPLE 1

Development of DNA Aptamers with an Affinity for his-Tag

Research into development of DNA molecules which have an affinity for molecular targets containing a His-tag, showed that DNA aptamers containing one of the following sequences have strong affinity:

(SEQ ID. No. 1)
5'-GTTTGCCGGTGGGCAGGTCTAGGGTCTGCTCGGGATTGCGGAGGAA
CATGCGTCGCAAAC-3', (SEQ ID. No. 2)
5'-GTTTGCCGGTGGGCAGGTTTAGGGTCTGCTCGGGATTGCGGAGGAA
CATGCGTCGCAAAC-3',

The invention allows DNA molecules to be obtained by any routine DNA synthesis method known to specialists.

To provide an example oligonucleotide molecules were obtained using chemical synthesis techniques in the solid phase (Zlatev, I., Manoharan, M., Vasseur, J.-J. and Morvan, F. Solid-Phase Chemical Synthesis of 5'-Triphosphate DNA RNA, and Chemically Modified Oligonucleotides. Current Protocols in Nucleic Acid Chemistry. 2012; 50:1.28.1-1.28.16.)

The aptamer A1 and B1 molecules obtained with the sequence above defined, a length of 60 nucleotides, and respectively synthesized in amounts of 641 and 612 micrograms were verified by the HPLC method. DNA molecules with these sequences may be subject to additional modifications. In particular, they may be used coupled with known dyes (e.g., fluorescent ones) or other molecules (e.g., biotin).

Example biotinylated aptamers A1 and B1, in amounts of 477 and 459 micrograms, were obtained by the automated synthesis of biotinylated oligonucleotides at 5'end. (Pon, R. T. A Long Chain Biotin Reagent for Phosphoramidite The Automated Synthesis of 5'-Biotinylated Oligonucleotides, Tetrahedron Lett. 1991; 32: 1715-1718). The products were verified by the HPLC method.

EXAMPLE 2

Binding of the his-Tag Protein to an Aptamer Bound Chromatographic Resin.

Figure 1:
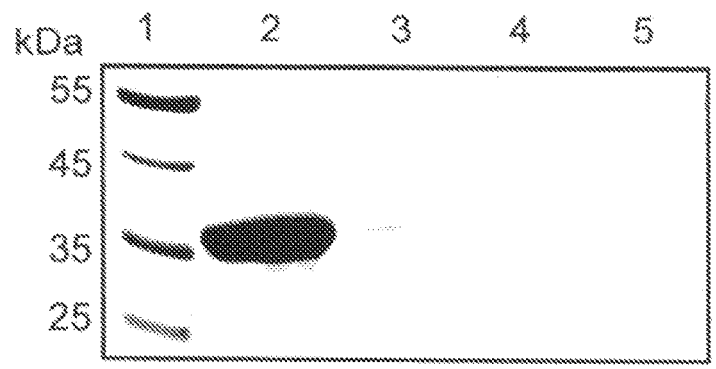
FIG. 1 shows binding between a protein containing a histidine tag and an aptamer. Lanes: 1) protein marker, 2) His-PCNA protein incubated with b1 aptamer, 3) PCNA protein incubated with b 1 aptamer, 4) His-PCNA protein incubated with a reference aptamer, 5) PCNA protein incubated with a reference aptamer. The samples were subjected to SDS-PAGE and then the proteins were stained in Coomassie Brilliant Blue R-250.

Ten µL of 50% agarose coupled streptavidin was placed in a 1.5 ml Eppendorf tube and washed with distilled water. Then it was washed three times with a BW buffer (17.5 g/L NaCl, 50 mM phosphate buffer $NaH_2PO_4/Na_2HPO_4$, 0.1% (v/v) TWEEN® 20 (polyethylene glycol sorbitan monolaurate), pH 7.5). Next, the resin was suspended in 300 µl of a BW buffer containing 20 µg of 5'-biotinylated either B1 or a reference aptamer. The samples were incubated at room temperature for 1h. After incubation, the resin was washed three times with the BW, followed by two washes with an AS buffer (137 mM NaCl, 12.7 mM KCl, 10 mM $Na_2HPO_4$, 2 mM $KH_2PO_4$, 5 mM $MgCl_2$, 0.1% (v/v) TWEEN® 20 (polyethylene glycol sorbitan monolaurate), pH 7.4). After the last washing, the resin with the bound aptamer was suspended in 300 µl of the AS buffer, and the recombinant human PCNA protein was added, to a final concentration of 0.13 mg/ml. In this experiment, two variants of the PCNA protein were used: a) with His-tag and b) without His-tag. The resin with the protein was incubated at room temperature for 1h. After incubation it was washed four times with the AS buffer, suspended in a GLB buffer (50 mM Tris-HCl, 2% SDS (w/v) bromophenol blue 2% (w/v), 10% glycerol, 200 mM β-mercaptoethanol, pH 6.8) and incubated for 5 min at 95° C. The resulting sample was subjected to SDS-PAGE (Laemmli method). After separation the proteins were stained using Coomassie Brilliant Blue R-250 dye. The results are shown in FIG. 1.

EXAMPLE 3

Purification of his-Tag Protein from a Protein Cell Extract.

Figure 2:
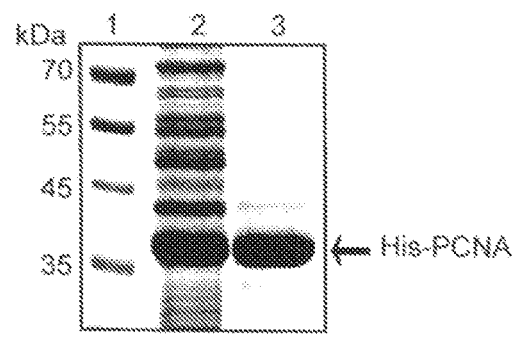
FIG. 2 shows the purification of a His-tag protein from an *E. coli* protein extract. Lanes: 1) protein marker, 2) 40 mg of *E. coli* protein extract 3) His-PCNA protein purified with the help of the B1 aptamer. The samples were subjected to SDS-PAGE and then the proteins were stained in Coomassie Brilliant Blue R-250.

Ten μof 50% agarose coupled streptavidin was placed in a 1.5 ml Eppendorf tube and washed with distilled water. Next, it was washed three times with a BW buffer (0.3 M NaCl, NaH$_2$PO$_4$/Na$_2$HPO$_4$ 50 mM phosphate buffer, 0.1% (v/v) TWEEN® 20 (polyethylene glycol sorbitan monolaurate), pH 7.5). The resin was suspended in 300 μl of the BW buffer containing 20 μg of 5'-biotinylated B1 aptamer and incubated at room temperature for 1h followed by three washes with the BW buffer and two with an AS buffer (137 mM NaCl, 12.3 mM KCl, 10 mM Na$_2$HPO$_4$, 2 mM KH$_2$PO$_4$, 5 mM MgCl$_2$, 0.1% (v/v) TWEEN® 20 (polyethylene glycol sorbitan monolaurate), pH 7.4;). After the last washing, the resin with the bound aptamer was suspended in 300 μl of the AS buffer. Next, the total protein extract prepared from *E. coli* cells overexpressing human recombinant His-PCNA protein was added to a concentration of 2.0 mg/ml. The resin was incubated at room temperature for 1h. After incubation, the resin was washed four times with the AS buffer. The His-PCNA was eluted with the help of an elution buffer (50 mM Tris, pH 7.5). The eluted proteins were mixed with a GLB buffer (50 mM Tris, 2% SDS (w/v) bromophenol blue 2% (w/v), 10% glycerol, 200 mM β-mercaptoethanol, pH 6.8) and incubated for 5 min at 95° C. The resulting sample was subjected to SDS-PAGE (Laemmli method). After separation the proteins were stained using Coomassie Brilliant Blue R-250. The results are shown in FIG. 2.

EXAMPLE 4

His-Tag Protein Detection Using the ELISA Method

Figure 3:
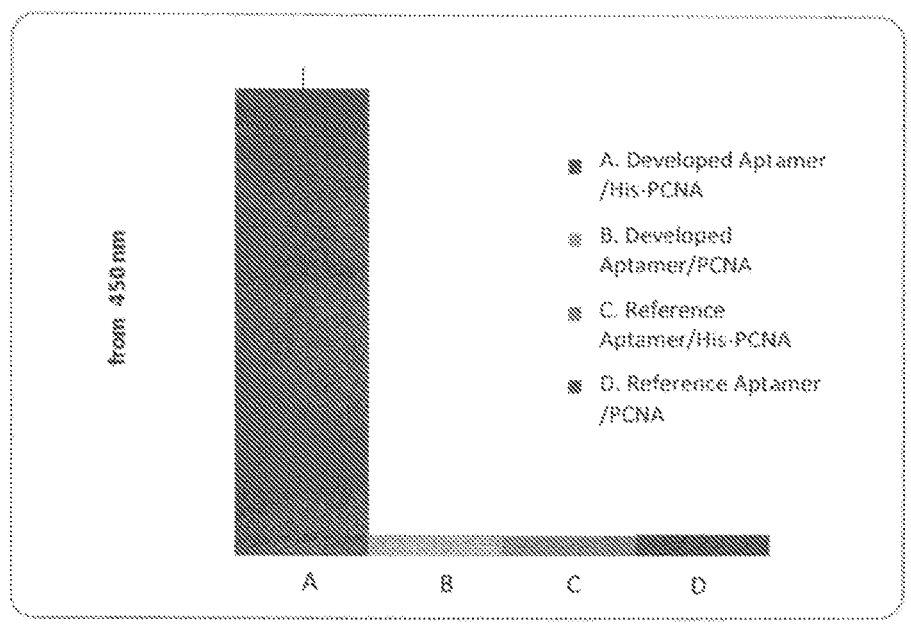
FIG. 3 presents the result of an ELISA test where the detection of recombinant protein containing the His-tag was done using a B1 aptamer. The data show the averaged result from three independent experiments.

A 96-well ELISA plate was coated with human PCNA protein (0.5 μg protein/well). In the experiment, two variants of the protein PCNA were used: a) with His-tag and b) without His-tag. The protein was bound to the plate for 16h at 4° C. Then, the plate was washed three times with an PBST (1×PBS containing 0.5% (v/v) TWEEN® 20 (polyethylene glycol sorbitan monolaurate)) buffer. Next, the plate was blocked in 1×PBS buffer containing 2% (w/v) bovine serum albumin for 2h at room temperature. In the following step the plate was washed three times with the PBST buffer and incubated with 5' biotinylated B1 or the reference aptamer in an AS buffer (137 mM NaCl, 12.3 mM KCl, 10 mM Na$_2$HPO$_4$, 2 mM KH$_2$PO$_4$, 5 mM MgCl$_2$, pH 7.4, 0.1% (v/v) TWEEN® 20 (polyethylene glycol sorbitan monolaurate) for one hour at room temperature. The final concentration of the aptamer was 0.01 mg/ml. After incubation the plate was washed three times using the PBST buffer and the plate was incubated with streptavidin coupled horseradish peroxidase (1:200 dilution in PBS buffer) for 40 minutes at room temperature. The plate was washed again three times with the PBST buffer, and then a horseradish peroxidase substrate was added to the wells. When the colour blue appeared, the reaction was stopped with 1M of H$_2$SO$_4$ and the absorbance was measured at a wavelength of 450 nm. The results are shown in FIG. 3.

The invention claimed is:
1. A DNA aptamer comprising a nucleotide sequence selected from the group consisting of SEQ ID NO: 1 and SEQ ID NO: 2, wherein the DNA aptamer binds a His-tag.

* * * * *

SEQUENCE LISTING

```
<160> NUMBER OF SEQ ID NOS: 2

<210> SEQ ID NO 1
<211> LENGTH: 60
<212> TYPE: DNA
<213> ORGANISM: artificial
<220> FEATURE:
<223> OTHER INFORMATION: aptamer A1

<400> SEQUENCE: 1
gtttgccggt gggcaggtct agggtctgct cgggattgcg gaggaacatg cgtcgcaaac      60

<210> SEQ ID NO 2
<211> LENGTH: 60
<212> TYPE: DNA
<213> ORGANISM: artificial
<220> FEATURE:
<223> OTHER INFORMATION: aptamer B1

<400> SEQUENCE: 2
gtttgccggt gggcaggttt agggtctgct cgggattgcg gaggaacatg cgtcgcaaac      60
```